United States Patent
Frisch et al.

(10) Patent No.: US 8,142,350 B2
(45) Date of Patent: Mar. 27, 2012

(54) IN-VIVO SENSING DEVICE WITH DETACHABLE PART

(75) Inventors: Mordechai Frisch, Moreshet (IL); Zvika Gilad, Haifa (IL); Gavriel J. Iddan, Haifa (IL); Arkady Glukhovsky, Santa Clarita, CA (US); Tal Davidson, Yoqneam Illit (IL); Daniel Gat, Haifa (IL); Raphael Rabinovitz, Raanana (IL)

(73) Assignee: Given Imaging, Ltd., Yoqneam (IL)

( * ) Notice: Subject to any disclaimer, the term of this patent is extended or adjusted under 35 U.S.C. 154(b) by 1337 days.

(21) Appl. No.: 10/585,053

(22) PCT Filed: Dec. 29, 2004

(86) PCT No.: PCT/IL2004/001183
§ 371 (c)(1),
(2), (4) Date: May 28, 2007

(87) PCT Pub. No.: WO2005/062717
PCT Pub. Date: Jul. 14, 2005

(65) Prior Publication Data
US 2007/0282164 A1    Dec. 6, 2007

Related U.S. Application Data

(60) Provisional application No. 60/533,227, filed on Dec. 31, 2003.

(51) Int. Cl.
*A61B 1/06* (2006.01)
*A61B 5/07* (2006.01)

(52) U.S. Cl. ...................................... 600/160; 600/302

(58) Field of Classification Search .................. 600/101, 600/109, 117, 118, 160
See application file for complete search history.

(56) References Cited

U.S. PATENT DOCUMENTS

| | | | |
|---|---|---|---|
| 3,683,389 | A | 8/1972 | Hollis |
| 3,683,890 | A | 8/1972 | Beal |
| 3,971,362 | A | 7/1976 | Pope et al. |
| 4,178,735 | A | 12/1979 | Jackson |
| 4,239,040 | A | 12/1980 | Hosoya et al. |
| 4,262,632 | A | 4/1981 | Hanton et al. |
| 4,278,077 | A | 7/1981 | Mizumoto |
| 4,439,197 | A | 3/1984 | Honda et al. |
| 4,560,286 | A | 12/1985 | Wickersheim |
| 4,646,724 | A | 3/1987 | Sato et al. |

(Continued)

FOREIGN PATENT DOCUMENTS

DE    34 40 177    5/1986
(Continued)

OTHER PUBLICATIONS

U.S. Appl. No. 09/571,326, filed May 15, 2000, Glukhovsky et al.
(Continued)

*Primary Examiner* — Philip R Smith
(74) *Attorney, Agent, or Firm* — Pearl Cohen Zedek Latzer, LLP (57) ABSTRACT

A device and system for in-vivo sensing having a relatively heavy part and a relatively light part such that the heavy and light part may be temporarily attached in-vivo. Detachment of the heavy part may be provided at a predetermined location along a body lumen. The light part upon detachment of the heavy part may for example float within a body lumen.

19 Claims, 5 Drawing Sheets

U.S. PATENT DOCUMENTS

| | | | |
|---|---|---|---|
| 4,689,621 A | 8/1987 | Kleinberg | |
| 4,741,327 A | 5/1988 | Yabe | |
| 4,803,992 A | 2/1989 | Lemelson | |
| 4,819,620 A | 4/1989 | Okutsu | |
| 4,844,076 A | 7/1989 | Lesho et al. | |
| 4,936,823 A | 6/1990 | Colvin et al. | |
| 4,940,997 A | 7/1990 | Hamlin et al. | |
| 5,187,572 A | 2/1993 | Nakamura et al. | |
| 5,267,033 A | 11/1993 | Hoshino | |
| 5,279,607 A | 1/1994 | Schentag et al. | |
| 5,318,557 A * | 6/1994 | Gross | 604/891.1 |
| 5,330,427 A | 7/1994 | Weissenburger | |
| 5,368,027 A | 11/1994 | Lubbers et al. | |
| 5,395,366 A | 3/1995 | D'Andrea et al. | |
| 5,398,670 A | 3/1995 | Ortiz et al. | |
| 5,437,274 A | 8/1995 | Khoobehi et al. | |
| 5,495,114 A | 2/1996 | Adair | |
| 5,549,109 A | 8/1996 | Samson et al. | |
| 5,558,640 A | 9/1996 | Pfeiler et al. | |
| 5,604,531 A | 2/1997 | Iddan et al. | |
| 5,697,384 A | 12/1997 | Miyakawi et al. | |
| 5,723,844 A | 3/1998 | Dow et al. | |
| 5,819,736 A | 10/1998 | Avny et al. | |
| 5,833,603 A | 11/1998 | Kovacs et al. | |
| 5,929,901 A | 7/1999 | Adair et al. | |
| 5,984,875 A | 11/1999 | Brune | |
| 5,986,693 A | 11/1999 | Adair et al. | |
| 5,993,378 A | 11/1999 | Lemelson | |
| 6,043,839 A | 3/2000 | Adair et al. | |
| 6,099,482 A | 8/2000 | Brune et al. | |
| 6,149,581 A | 11/2000 | Klingenstein | |
| 6,228,048 B1 | 5/2001 | Robbins | |
| 6,233,476 B1 | 5/2001 | Stormmer et al. | |
| 6,240,312 B1 | 5/2001 | Alfano et al. | |
| 6,324,418 B1 | 11/2001 | Crowley et al. | |
| 6,632,175 B1 | 10/2003 | Marshall | |
| 6,692,430 B2 | 2/2004 | Adler | |
| 6,929,636 B1 * | 8/2005 | von Alten | 604/890.1 |
| 2001/0017649 A1 | 8/2001 | Yaron | |
| 2001/0025135 A1 | 9/2001 | Naito et al. | |
| 2001/0035902 A1 | 11/2001 | Iddan et al. | |
| 2001/0051766 A1 | 12/2001 | Gazdzinski | |
| 2002/0103417 A1 | 8/2002 | Gazdzinski | |
| 2002/0146368 A1 | 10/2002 | Meron et al. | |
| 2002/0158976 A1 | 10/2002 | Vni et al. | |
| 2002/0177779 A1 | 11/2002 | Adler et al. | |
| 2002/0198439 A1 | 12/2002 | Mizuno | |
| 2003/0018280 A1 * | 1/2003 | Lewkowicz et al. | 600/549 |
| 2003/0023150 A1 * | 1/2003 | Yokoi et al. | 600/300 |
| 2003/0028078 A1 | 2/2003 | Glukhovsky et al. | |
| 2003/0045790 A1 | 3/2003 | Lewkowicz et al. | |
| 2003/0114742 A1 | 6/2003 | Lewkowicz et al. | |
| 2003/0117491 A1 | 6/2003 | Avni et al. | |
| 2003/0120130 A1 * | 6/2003 | Glukhovsky et al. | 600/109 |
| 2003/0167000 A1 | 9/2003 | Mullick et al. | |
| 2003/0171648 A1 | 9/2003 | Yokoi et al. | |
| 2003/0171649 A1 | 9/2003 | Yokoi et al. | |
| 2003/0171652 A1 | 9/2003 | Yokoi et al. | |
| 2003/0195415 A1 | 10/2003 | Iddan | |
| 2003/0208107 A1 | 11/2003 | Refael | |
| 2003/0214579 A1 | 11/2003 | Iddan | |
| 2003/0214580 A1 | 11/2003 | Iddan | |
| 2003/0216622 A1 * | 11/2003 | Meron et al. | 600/300 |
| 2004/0027459 A1 | 2/2004 | Segawa et al. | |
| 2004/0068204 A1 * | 4/2004 | Imran et al. | 600/593 |
| 2004/0111011 A1 * | 6/2004 | Uchiyama et al. | 600/160 |
| 2004/0133076 A1 * | 7/2004 | Kobayashi et al. | 600/175 |
| 2006/0004255 A1 * | 1/2006 | Iddan et al. | 600/160 |
| 2006/0020171 A1 * | 1/2006 | Gilreath | 600/188 |

FOREIGN PATENT DOCUMENTS

| | | |
|---|---|---|
| FR | 2 688 997 | 10/1993 |
| IL | 143259 | 5/2001 |
| JP | 57-45833 | 3/1982 |
| JP | HEI 3-289779 | 12/1991 |
| JP | 4109927 | 4/1992 |
| JP | HEI 4-109927 | 4/1992 |
| JP | 1992-144533 | 5/1992 |
| JP | 4144533 | 5/1992 |
| JP | HEI 4-180736 | 6/1992 |
| JP | 5015515 | 1/1993 |
| JP | 6114037 | 4/1994 |
| JP | 6285044 | 10/1994 |
| JP | 7111985 | 5/1995 |
| JP | 7289504 | 11/1995 |
| JP | 2000342522 | 12/2000 |
| JP | 2001091860 | 4/2001 |
| JP | 2001095755 | 4/2001 |
| JP | 2001095756 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001112709 | 4/2001 |
| JP | 2001112710 | 4/2001 |
| JP | 2001112740 | 4/2001 |
| JP | 2001137182 | 5/2001 |
| JP | 2001224551 | 8/2001 |
| JP | 2001224553 | 8/2001 |
| JP | 2001231744 | 8/2001 |
| JP | 2001245844 | 9/2001 |
| JP | 2000342524 | 6/2002 |
| JP | 2000342525 | 6/2002 |
| WO | WO 92/21307 | 12/1992 |
| WO | WO 98/11816 | 3/1998 |
| WO | WO 00/22975 | 4/2000 |
| WO | WO 01/10291 | 2/2001 |
| WO | WO 01/50941 | 7/2001 |
| WO | WO 01/53792 | 7/2001 |
| WO | WO 01/65995 | 9/2001 |
| WO | WO 01/69212 | 9/2001 |
| WO | WO 02/26103 | 4/2002 |
| WO | WO 02/054932 | 7/2002 |
| WO | WO 02/055126 | 7/2002 |
| WO | WO 02/067593 | 8/2002 |
| WO | WO 02/094337 | 11/2002 |
| WO | WO 03/003706 | 1/2003 |
| WO | WO 03/011103 | 2/2003 |
| WO | WO 2004/028336 | 4/2004 |
| WO | WO 2004/035106 | 4/2004 |

OTHER PUBLICATIONS

U.S. Appl. No. 09/807,892, filed Jun. 6, 2001, Meron et al.

U.S. Appl. No. 10/200,548, filed Jul. 23, 2002, Glukhovsky et al.

U.S. Appl. No. 10/724,109, filed Dec. 1, 2003, Glukhovsky et al.

Shin-Ichi, et al.: "Robots for the Future", Nov. 29, 2001.

"Video Camera to TAKE", RF System Lab, Dec. 25, 2001.

Wang, et al.: "Integrated Micro-Instrumentation for Dynamic Monitoring of the Gastro-Intestinal Tract", Presented at IEEE Instrumentation and Measurement Technology Conference, May 2002, Anchorage, AK, USA, www.see.ed.ac.uk/Naa.publications.html.

www.rfnorkia.com-NORIKA3, Dec. 24, 2001.

Crum: "Wellesley Company sends body monitors into space", Boston Business Journal, 1998.

Rowlands et al: "The Radio Pill", British Communications and Electronics, Aug. 1960, pp. 598-601.

Swain, CP and Gong, F.: "Wireless transmission of a color television moving image from the stomach using a miniature CCD camera, light source and microwave transmitter", Gastrointestinal Endoscopy, 1997, 45:AB40.

BBC News Online—"Pill camera to 'broadcast from the gut'", Feb. 21, 2000, www.news.bbc.co.uk.

The Heidelburg pH Capsule System Telemetric Fasting Gastric Analysis, Heidelburg International Incorporated.

Lange et al: "Heidelberger Kapsei-ein Kleinstsender fur die pH-Messung im Magen", Telefunken-Zeitung, Jg 36 (1963) Heft 5, pp. 265-270.

"New Smart Plastic has Good Memory", Turke, European Medical Device Manufacturer, devicelink.com.

Craford et al: "In Pursuit of the Ultimate Lamp", Scientific American, Feb. 2001.

Manual of Photogrammetry. Thompson (Ed.), Third Edition, vol. Two, Copyright 1944, 1952, 1966 by the American Society of Photogrammetry.

www.jason.net/tinycam.htm, © 2001, printed Dec. 19, 2001.

"Review proves the value computers", © 2001, www.middleeasthealthmag.com/article2.htm, printed Nov. 29, 2001.

www.pedinc.com, Personal electronic devices, © 1997.

International Search Report dated Oct. 17, 2005 for Application No. PCT/IL04/01183.

U.S. Appl. No. 10/540,890, filed Feb. 23, 2006, Gilad et al.
U.S. Appl. No. 11/024,906, filed Dec. 30, 2004, Frisch et al.
U.S. Appl. No. 11/025,124, filed Dec. 30, 2004, Iddan et al.
U.S. Appl. No. 10/166,025, filed Jun. 11, 2002, Lewkowicz et al.
U.S. Appl. No. 10/213,345, filed Aug. 7, 2002, Glukhovsky et al.

* cited by examiner

IN-VIVO SENSING DEVICE WITH DETACHABLE PART

The present application is a national phase application of International Application PCT/IL2004/001183, entitled "IN-VIVO SENSING DEVICE WITH DETACHABLE PART" filed on Dec. 29, 2004, which in turn claims priority from U.S. provisional application serial number 60/533,227, filed on Dec. 31, 2003, entitled "IN-VIVO SENSING DEVICE WITH DETACHABLE PART", all of which are incorporated by reference in their entirety.

FIELD OF THE INVENTION

The present invention relates to the field of in-vivo sensing. Specifically, the present invention relates to a floatable in-vivo sensing device with a detectable part.

BACKGROUND OF THE INVENTION

An in-vivo device such as an ingestible sensing device may be used for sensing in-vivo conditions in cavities or body lumens such as for example the gastrointestinal (GI) tract. Parameters that may be sensed or detected include for example temperature, pH, pressure, electroconnectivity, etc. In-vivo imaging devices may be used for imaging of body lumens such as the GI tract. For example, an ingestible capsule including a sensor, such as an image sensor, may be ingested and may move through the small intestine by peristalsis while imaging or otherwise sensing the small intestine. However, passive movement of objects such as for example imaging sensors, such as by way of peristalsis through larger body lumens, such as the large intestine, may be slow and unpredictable and may not facilitate proper imaging of such larger body lumens.

The large intestine or colon, whose main function is to remove much of the water from the stool and to store the stool, begins with the cecum, a small saclike evagination, then continues with the ascending colon, from the appendix in right groin up to a flexure at the liver, transverse colon, liver to spleen, descending colon, spleen to left groin, then sigmoid (S-shaped) colon back to midline and anus. The colon has three longitudinal muscle bands whose actions assist movement through the colon.

SUMMARY OF THE INVENTION

Embodiments of the invention describe an in-vivo sensing device that may be for example floatable or have a certain buoyancy or specific gravity in some parts of a lumen and be non-floating or have a certain other buoyancy or specific gravity in other parts of the lumen. The in-vivo device may have a floatable and/or relatively light part and/or a non-floatable and/or relatively heavy part that may be temporarily attached. In a part of the lumen where it may be desirable for the in-vivo device to have floatable qualities the light part and the heavy part of the in-vivo device may disengage. In some embodiments of the present invention, the disengagement may initiate a component in the in-vivo device to activate. In other embodiments of the present invention one or more sensors may be used to detect the position along the lumen where it may be desirable to disengage the light and heavy part of the in-vivo device.

BRIEF DESCRIPTION OF THE DRAWINGS

The present invention will be understood and appreciated more fully from the following detailed description taken in conjunction with the drawings in which.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

According to some embodiments of the present invention, there may be provided an in-vivo sensing device that may be configured to for example alter configurations so that at a particular times or in particular areas or body lumens, such as for example the small intestine, the device may be or include a substantially floating or buoyant device, while at other times or at other areas or body lumens such as for example parts of the large intestine, the device may be a substantially non-floating device.

A substantially floatable or floatable in-vivo sensing device may float in or be carried by liquids and/or bodily fluids in for example a body lumen. For example, in one embodiment, the liquid contained in a body lumen, such as a GI tract, may have a specific gravity of approximately one, and thus a floatable device or portion of a device may have a specific gravity of less than one. In other embodiments, the specific gravity of the liquid and/or bodily fluid contained in the body lumen may be greater or less than one and the specific gravity of the floatable device may be less than the specific gravity of the liquid contained in the body lumen. Such sensing device may be useful in sensing, such as by imaging, lumens containing or capable of containing a bulk of liquid. One example of such a lumen may be the large intestine or colon. A floatable sensing device may, for example, be carried by the liquid in the large intestine and may thus be moved through the lumen together with the bulk of liquid.

It may be advantageous to move objects through a body lumen, for example, the colon independently of the natural action of the body lumen muscles. For example, delivery of a medicament to a specific location in the colon may be time dependant, such that the natural movement in the colon may not be sufficiently reliable to deliver such medicaments on time. Also a device for imaging the colon might benefit from being moved, such as by way of floating, through the colon so as to efficiently view the colon.

While a floating in-vivo sensing device may be useful in lumens with a bulk of liquids such as for example in certain parts of the colon, a floating in-vivo sensing device may be less than optimal for sensing of other areas of the GI tract, such as for example the small intestine. Furthermore, a floating in-vivo sensor may typically traverse the GI tract relatively slowly. Thus, an internal power supply (e.g., a battery) may be depleted before the floatable sensor may reach the end of the GI tract.

In some embodiments, a sensing device in accordance with an exemplary embodiment of the invention may be an ingestible sensing device. Embodiments of an ingestible imaging device may be described in U.S. Pat. No. 5,604,531 to Iddan et al. and in U.S. application Ser. No. 09/800,470, entitled "A Device And System For In-vivo Imaging", file on 8 Mar. 2001, both of which are assigned to the common assignee of the present application and incorporated herein by reference. Embodiments of a floatable sensing device are described in U.S. patent application Ser. No. 10/150,492, which was published under the publication number 20030018280 on Jan. 23, 2003 and which is assigned to the assignee of the present invention and which is hereby incorporated by reference. Various embodiments of the present invention may use or may be used with devices and methods, such as imaging and/or receiving devices and methods, as described in U.S. Pat. No. 5,604,531 and/or U.S. Ser. No. 09/800,470 and or US 20030018280, however other embodiments may use methods and have structures not found in these references.

Figure 1:
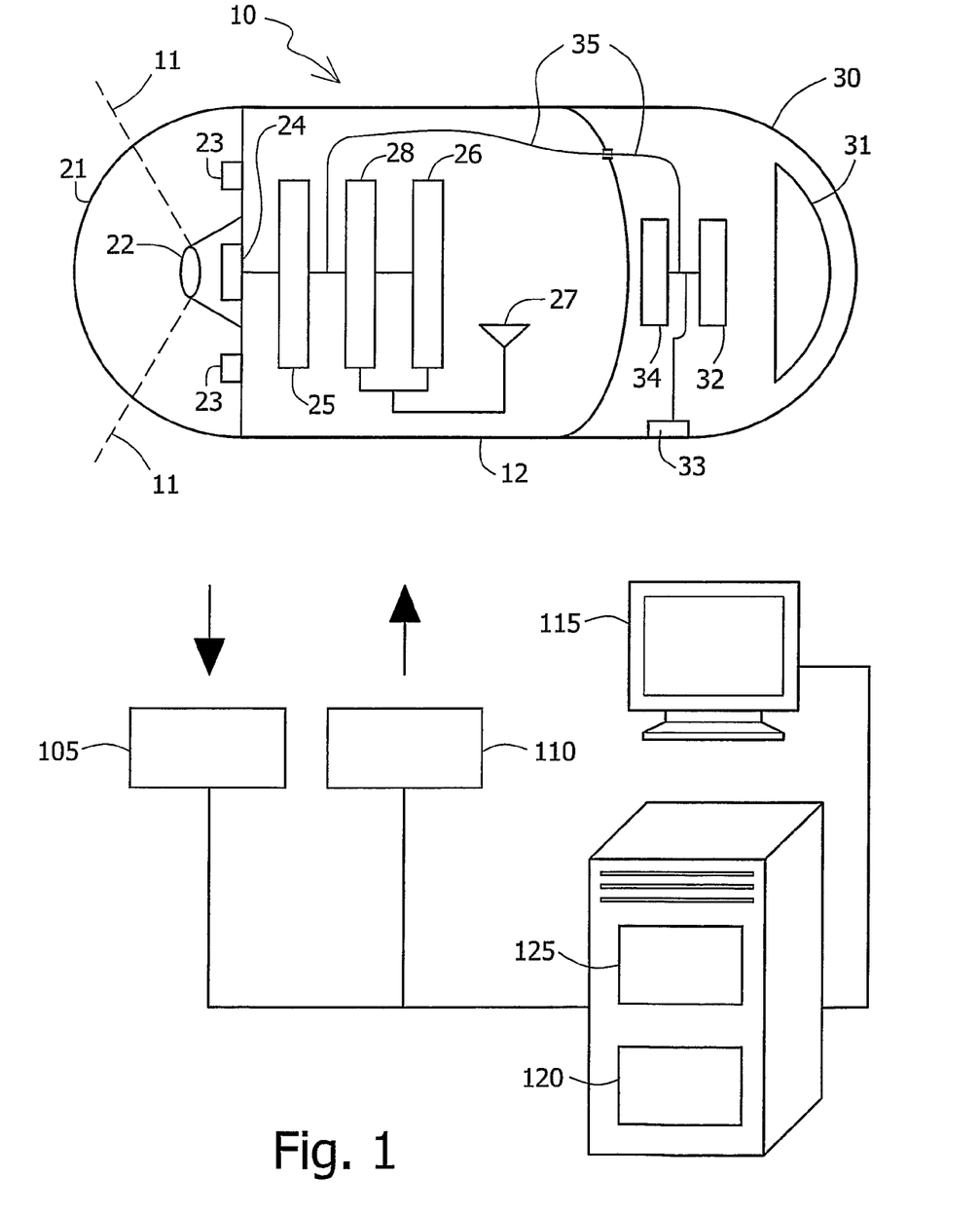
FIG. 1 is an illustration of an in-vivo sensing system with an in-vivo device having a detachable heavy part and a light part in accordance with an exemplary embodiment of the invention.

Reference is now made to FIG. 1, an illustration of an in-vivo sensing system with an in-vivo device having a detachable relatively heavy part and a relatively light part, in accordance with an exemplary embodiment of the invention. Device 10 may be a sensing device such as for example an autonomous in-vivo imaging device. In some embodiments device 10 may include for example other sensors instead of or in addition to an imaging sensor, such as for example a temperature sensor, a pH sensor, a pressure sensor or an electrical conductivity sensor. Other sensors are possible. For example, a motion detector may be included in device 10 for determining, for example, when the device may be in motion; external motion detection may be used as well.

In some embodiments device 10 may include for example an optical and/or viewing window 21 and an imaging system for obtaining image data from inside a body lumen. The imaging system may include for example one or more illumination sources 23, such as for example a white LED or another illumination source that may illuminate in another color or use some other electromagnetic frequency. Device 10 may for example include an imager such as, for example, an imager 24, which may detect images, and an optical system 22, which may include, for example, a lens and a lens holder, which may for example focus images onto, for example, the imager 24. In one embodiment, imager 24 may be a CMOS imager, however, other types of imagers such as for example a CCD or other imagers may be used. Illumination source 23 may illuminate for example a body lumen through optical window 21. Device 10 further may include circuitry such as for example an ASIC transmitter 26 and an antenna 27 that may for example transmit signals, and a power source 25, such as for example silver oxide batteries, that may for example provide power to the electrical elements of device 10. Signals that may be transmitted by for example transmitter 26 may include video, still images, temperature, pH or other sensory data as may be collected by device 10. In some embodiments of the present invention transmitter 26 may include control circuits for controlling one or more functions of device 10. In other embodiments device 10 may include a receiver 28 for receiving external commands or signals. In some embodiments of the present invention the receiver 28 may and transmitter 26 may be integrated into a transceiver.

Device 10 may be shaped, for example, as a cylinder with convex ends, as a sphere or in other shapes or dimensions as may be suitable for passage in or through a body lumen. Device 10 may in some embodiments be shaped as an oval or capsule. Other shapes may be used.

In some embodiments, device 10 may be configured for example in two or more lobes or parts, which may be, for example, releasably held together such that such parts may be detached for example under certain conditions, upon the occurrence of certain events, or upon sensing one or more parameters for example that may be above a determined threshold. One of such parts may for example be a floating, buoyant or light part 12 and another may be a non-buoyant or heavy part 30. In some embodiments, the terms light and heavy may be relative terms with respect to buoyancy and not necessarily with respect to the absolute weight of a light part 12 as compared to a heavy part 30. In some embodiments the relatively light part 12 may be releaseably connected to the relatively heavy part 30 so that heavy part 30 may be detachable from light part 12. In some embodiments, light part 12 may include or contain some or all of the device's 10 active or functional components, for example, components that may be required for in-vivo sensing, e.g. possibly including optical system 22, ASIC transmitter/controller 26, power source 25 and antenna 27, such that for example light part 12 may be self contained, being capable of performing sensory and transmitting functions after it detaches from heavy part 30. The specific gravity for light part 12 may be reduced, for example to a specific gravity less than the specific gravity of bodily fluids present in a body lumen, by, for example, providing a volume of empty space, by for example increasing the volume of light part 12 above the minimal volume required to enclose the elements incorporated within the housing of light part 12. The additional volume may be dispersed between the components or concentrated in the central area of light part 12 or may be concentrated between the viewing dome 21 and the image sensor 24, or in other suitable areas. In one embodiment, an additional volume may be incorporated by elongating cross-section area of device 10 so as to create an elliptical cross-section and thus increase the cross-sectional area and volume of light part and/or device 10 so as to reduce the specific gravity of light part 12. A device, such as a capsule with an elliptical cross-section may be easier to swallow than a device with a similar volume having a circular cross-section. In some embodiments, heavy part 30 may also include for example one or more components electrical or otherwise, for example sensors 33 such as for example an imager, a pH sensor, a thermometer or other sensor, a power source 32 such as for example a battery or other components, so that heavy part 30 may for example perform sensing functions before or after it detaches from light part 12 or independently of light part 12. In some embodiments sensor 33 may be linked by for example wires 35 or other circuitry or by wireless electrical communication to the ASIC transmitter/controller 26 and antenna 27 of light part 12 so that sensory data collected by heavy part 30 may be transmitted through antenna 27 while heavy part 30 and light part 12 may be attached, for example, temporarily attached. In some embodiments, heavy part 30 may include a transmitter and circuitry 34 so that it may broadcast sensory data, for example, after it may be detached from light part 12.

Heavy part 30 may be configured to have on its own or together with or when connected to light part 12 a specific gravity above the specific gravity of the in vivo body lumen liquid, or for example above 20 percent more, and/or a specific gravity that may renders it at least substantially non-floatable in for example an in-vivo environment. Typically, according to some embodiments of the inventions when heavy part 30 may be connected to or temporarily attached to light part 12, device 10 may generally not be buoyant or floatable in water or other fluids as may be present in for example a body lumen such as for example the GI tract. Heavy part 30 may, in some embodiments, be weighted with one or more ballast(s) or weight(s) 31 of for example metal, plastics or some other suitable material or may for example have a thicker shell or may be solid part. The size of heavy part 30 may in some embodiments be up to approximately one third the size of device 10, though other sizes and ratios may be possible. Heavy part 30 may have specific gravity that is other than the specific gravity of light part 12.

Light part 12 may be weighted or configured to have a specific gravity of less than or approximately 1 in water or other fluids found in a body lumen, such that light part 12 (typically without heavy part 30 attached to it) may float in body fluids or other fluids, such as water. In some embodiments light part 12 may be weighted for example evenly around one or more of its internal axis so that when it floats in a liquid it may not favor a particular orientation, but may rotate or otherwise move relatively freely in surrounding water or other fluids. In some embodiments, light part 12 may be weighted, or may have components or weights or lighter parts arranged in such a manner (e.g., a ballast on one end and/or a gas reservoir or other light unit on, for example, the opposite end), to favor a particular orientation so that it may for example return to a favored orientation even after it is moved or rotated away from such favored orientation.

In some embodiments, light part 12 may have s specific gravity of for example, less than 0.9 or less than 0.7. In some embodiments, heavy part 30 may have s specific gravity of for example, greater than 1.1 or greater than 1.3.

In some embodiments and in an initial state when for example device 10 may be ingested or otherwise inserted into a body, light part 30 and heavy part 12 may be temporarily attached to each other and device 10 may therefore assume a non-buoyant configuration. In some embodiments, device 10 may be propagated or moved passively by way of peristalsis or otherwise through a body lumen such as for example the stomach or small intestine, in such non-buoyant configuration.

In some embodiments, at a particular time, or at a particular point in a body lumen or in response to for example a signal, environmental condition and/or parameter that may be sensed by one or more sensors or the passage of time, light part 12 may separate or detach from heavy part 30 and light part 12 may assume a buoyant or floating configuration. In some embodiments the detaching of light part 12 from heavy part 30 may occur or be initiated for example at or near the point where device 10 approaches or enters the cecum, a small sac-like formation before the colon. Other points for such detaching or release may be designated and may be achieved. In some embodiments, the configuration, weight or specific gravity of device 10 before heavy part 30 may be detached from light part 12 may cause device 10 to settle for example in or near the cecum, where the detachment of heavy part 30 from light part 12 may take place.

A detached heavy part 30 may in some embodiments continue sensing or collecting data and possibly transmitting data to an external receiver 105. In some embodiments detached heavy part 30 may be excreted from a body by, for example, peristaltic contraction or due to other natural or other processes.

External from the device 10 an external receiver 105 may receive signals, for example, wireless signals from device 10. Reception may be accomplished via a radio frequency (RF) wireless channel. Other suitable methods of reception may be possible. Storage unit 125 may store signals received by external receiver 105, for example, image data, sensor data, control data, etc. Processor 120 may process data, for example, to perform analysis and to display, for example, on a display 115. External transmitter 110 may transmit control signals or other signals to device 10. Transmitter 110 may be a RF transmitter, an ultrasound transmitter or other suitable transmitter. Transmitter 110 may be used to external control device 10, for example, to control the detaching of light part 12 and heavy part 30. Transmitter 110 may be used to control other functionalities of device 10.

Figure 2:
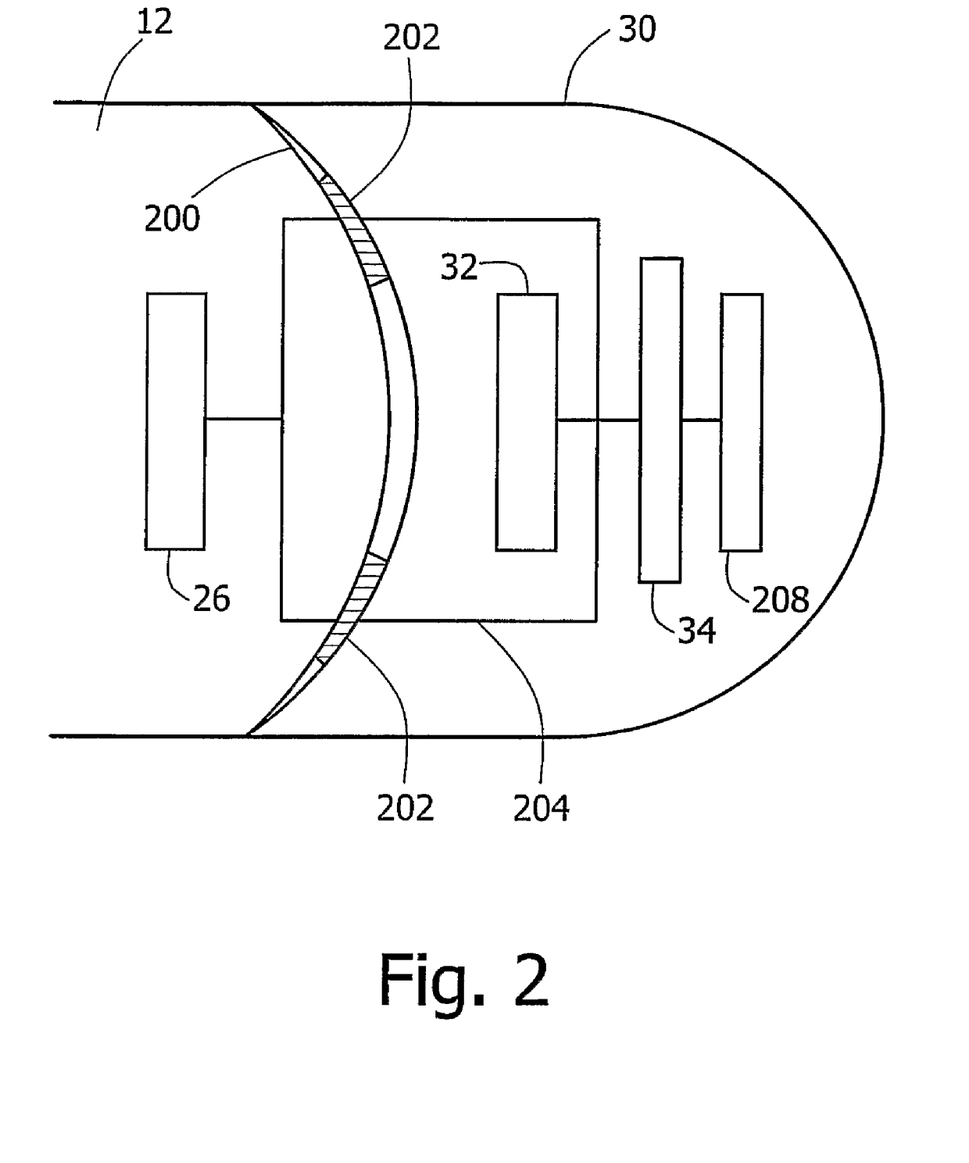
FIG. 2 is a schematic illustration of an area of an in-vivo sensing device where a heavy part and a light part of such device may be connected in accordance with an exemplary embodiment of the invention.

Reference is made to FIG. 2, a schematic illustration of an area of an in-vivo sensing device where a heavy part and a light part of such device may be connected. In some embodiments, light part 12 and heavy part 30 may be attached for example along a surface 200 which may in some embodiments be near or include an end or pole of light part 12. Surface 200 which may be for example along the edge of light part 12, may in some embodiments be convex so that when heavy part 30 may be detached from light part 12, light part 12 assumes or retains a capsule or oval shape. Surface 200 along the edge of heavy part 30 that may be close to light part 12 may be concave or in a half moon shape so that is fits smoothly into light part 12. Other shapes such as for example a wave that alternates between convex and concave, are possible and other planes along which heavy part 30 and light part 12 may be attached are possible.

Heavy part 30 and light part 12 may be attached or releasably and/or detachably held together by a fastener 202 such as for example glue, fuses, wires, magnets or other fastening means or combination of fastening means that may detachably hold and then later release heavy part 30 from light part 12. Detachably holding may mean for example holding an item until such time as the hold is released or until a trigger, event or condition may facilitate the release of the item.

In an exemplary embodiment of the invention, fastener 202 may be freed or is may release a releasably held item such as for example heavy part 30, in response to, for example, a signal or in response to the passage of time or in response to one or more environmental conditions. For example, fastener 202 may be or may include a wire or filament such as for example a fuse or heat sensitive or degradable filament. In some embodiments, in response to a signal, heat may be applied to or a current may be passed through fastener 202 such as for example a heat sensitive filament or fuse, and heat sensitive filament or fuse may melt or degrade, freeing or allowing the detaching of heavy part 30 from light part 12. In some embodiments of the present invention heat, an electrical charge, or a force may be applied to a fastener 202 by for example wires 204 connected to power source 32 or power source 25 or some other power supply.

In some embodiments fastener 202 may be for example one or more magnets, magnetized materials or materials that are responsive to an electromagnetic force. Upon or in response to a signal, or at other times, such magnets may be deactivated or otherwise released, by for example reversing the polarity of an electromagnet and/or changing the direction of the electromagnetic field, thereby freeing or detaching heavy part 30 from light part 12.

In still other embodiments, fastener 202 may be a degradable filament or glue that may degrade over the course of, for example, the several hours or other time period in which device 10 may be in a body before it reaches a designated body lumen such as for example the large intestine. In some embodiments such period may be from 6 to 8 hours. Such degradation may be precipitated by for example exposure to body temperatures, exposure to certain liquids, pH levels or other elements or conditions as may be present in a body lumen. In some embodiments the thickness or other characteristics of a fastener 202 such as for example a degradable filament or glue may be configured to degrade over a period of time that may approximate the period required for device 10 to travel or be moved from for example the mouth to for example the cecum or some other desired location. Other configurations may be possible and other time periods or degradation triggers or criteria may be used.

Other methods or processes for releasing fastener 202 such as for example by the release of a chemical that may degrade fastener 202, from for example a portion of light part 12 or heavy part 30 along for example surface 200, are possible. In some embodiments, heavy part 30 or light part 12 may encapsulate medicaments or other materials that may be released when heavy part 30 detaches from light part 12. In other embodiments of the present invention, heavy part 30 may not detach and may instead release encapsulated material, e.g. degradable material, medicaments, or independent component. In some embodiments of the present invention, emptying attached heavy part 30 may enable device 10 to become substantially buoyant. As such heavy part 30 may not be detachable.

The detaching of heavy part 30 from light part 12 may in some embodiments be precipitated or initiated by for example a signal. In some embodiments, a signal may be generated by for example circuitry 34 or ASIC transmitter/controller 26. In some embodiments, a signal may be generated for example in response to a timer 208 or counter that may be included in for example circuitry 34 or ASCI transmitter/controller 26 or elsewhere, and such timer may be set to generate a signal after for example the lapse of time that may approximate the amount of time required for device 10 to proceed from for example the mouth to for example the cecum. Other time periods are possible. In some embodiments timer 208 may be activated when for example device 10 is ingested or when for example device 10 is removed from its packaging prior to ingestion. In other embodiments timer 208 may be activated upon detection of a is specified site in the GI tract.

In some embodiments a signal may be initiated from a source external to device 10 such as for example a transmitter located outside of a body. Such signal may be received by or may otherwise affect a component of device 10. For example, device 10 may include a receiver 26 that may receive a signal from a transmitter outside of a body. Such receiver 26 may initiate for example a pulse of heat, electricity or magnetic charge to release fastener 202, thereby detaching heavy part 30 from light part 12. In other embodiments a signal may be generated by, for example, an ultrasound transmitter and/or mechanism that may be located outside of a body and that may direct ultrasound waves towards a fastener 202, such as for example a filament that is sensitive to ultrasound waves. Other signals that may precipitate a release of fastener 202 and the detaching of heavy part 30 and light part 12 are possible. In some embodiments, ultrasound waves may be directed at device 10 or heavy part 30 and such ultrasound waves may detach or otherwise break apart heavy part 30. In other embodiments, a part of heavy part 30 may disintegrate, dissolve or otherwise degrade thus releasing it from light part 12.

In some embodiments the sensors or sensing devices of device 10 may, until heavy part 30 separates from light part 12, be inactive, set to off or may operate at a reduced rate or under reduced power consumption levels. In an exemplary embodiment, the detachment or separation of heavy part 30 from light part 12 may trigger or serve as a signal for device 10 to activate, change functionality, or turn on, or for one or more sensors of light part 12 to begin collecting sensory data such as for example images. The turning on of device 10 or of sensors in light part 12 that may begin for example with the separation or detachment of heavy part 30, may for example preserve the power available to light part 12 in, for example, power supply 25 so that sufficient power remains in such power supply 25 or in light part 12 to power sensors and collect sensory data from body lumens, such as for example some or all of the large intestine wherein light part 12 may be set afloat.

Figure 3:
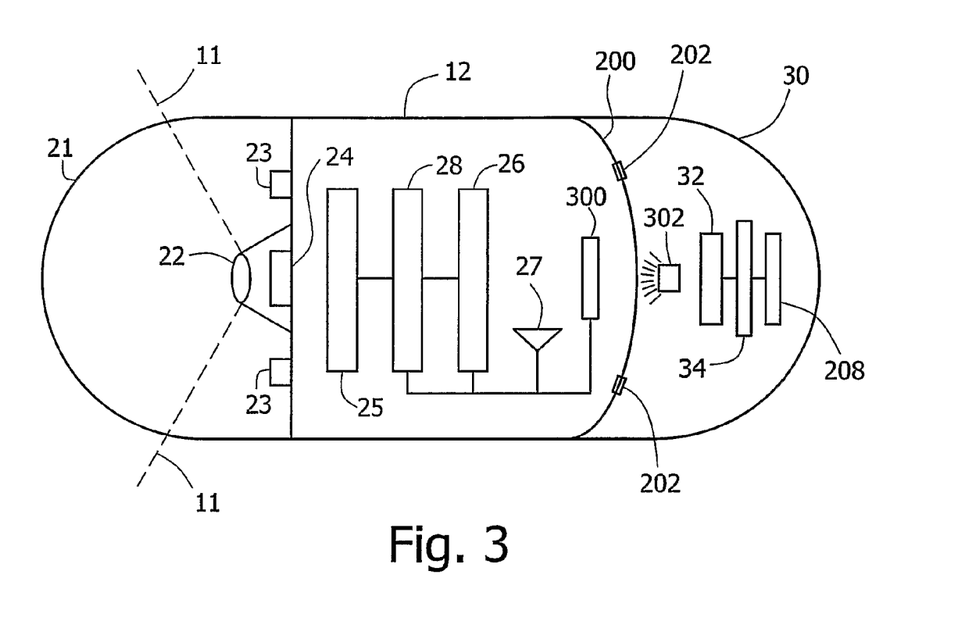
FIG. 3 is a schematic illustration of an in-vivo device with a switch and a detachable part in accordance with an exemplary embodiment of the invention.

Reference is made to FIG. 3, a schematic illustration of an in-vivo device with a photodiode switch and a detachable portion in accordance with an exemplary embodiment of the present invention. The device 10 depicted in FIG. 3 may include, for example, a switch 300 such as for example a photodiode switch on or near surface 200 and an illumination device 302 such as for example a light emitting diode (LED) that may also be situated on or near, and facing surface 200. In some embodiments switch 300 may be situated in light part 12 and illumination device 302 may be situated in heavy part 30. In other embodiments, switch 300 and illumination device 302 may be situated elsewhere in device 10 and may be connected to for example power source 32 and/or power source 25. In some embodiments, surface 200 may be made for example from a transparent material or may otherwise be transparent or semi-transparent to the light emitted by illumination device 302. In some embodiments of the present invention, illumination device 302, not be incorporated into device 10 and may be external to the body lumen, for example, may be placed over the skin such that light from illumination device 302 may penetrate through the skin, for example, illumination device 302 may be positioned directly over the cecum and the light may be detected by photodiode switch 300. In one example, photodiode switch 300 may trigger one or more components in light part 12 and/or heavy part 30 to, for example, activate.

In some embodiments, in response to a signal such as for example a signal from a counter such as for example timer 208 or another suitable counter or another suitable signal, illumination device 302 may emit light or otherwise signal switch 300 with for example light that may be detected by switch 300. Such signal as received by switch 300 may trigger, activate or otherwise turn on one or more sensing devices or other components of light part 12 or device 10. A counter such as for example timer 208 may also signal a power source such as for example power source 25 or power source 32 to provide a pulse of for example, heat or electricity that may release or burn fastener 202 such as for example wires, fuses or filaments, thus detaching heavy part 30 from light part 12.

In some embodiments of the present invention, imager 24, optical system 22, and/or illumination 23 may be positioned away from viewing window 21 as compared to corresponding components shown, for example, in FIG. 1. The volume between, for example, imager 24 and viewing window 21 may serve as the additional volume that may be required to decrease the specific gravity of light part 12 as may be described herein and may also serve to increase the viewing area on viewing window 21 that may be defined by viewing lines 11 (compare to the field of view of FIG. 1), so that imager 24 may capture, for example, more the periphery of body lumen.

Figure 4:
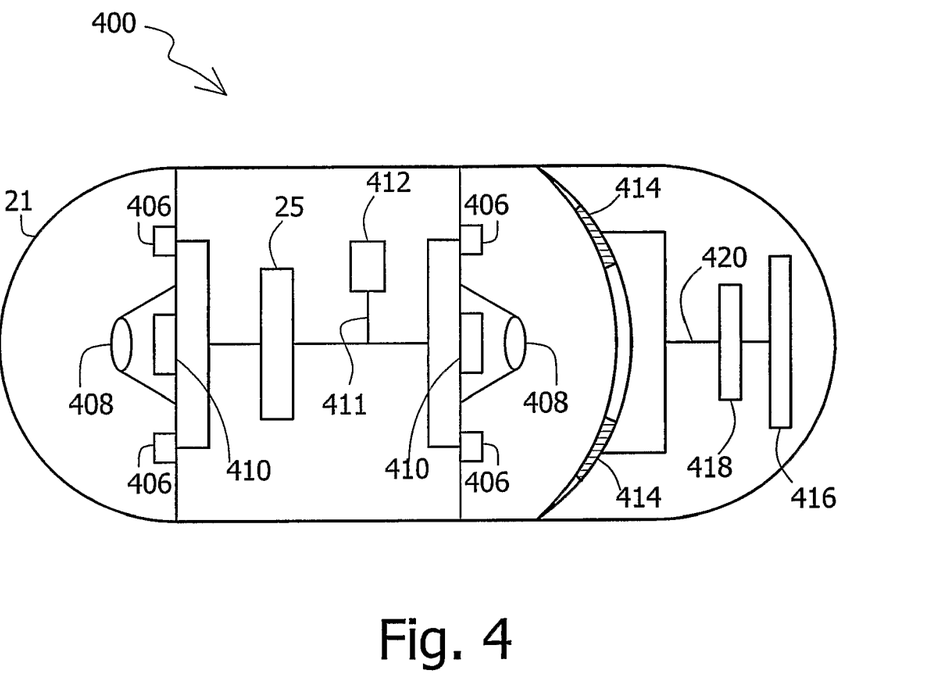
FIG. 4 is a schematic illustration of an in-vivo device with at least one sensor, a switch and a detachable part in accordance with an exemplary embodiment of the invention.

Reference is made to FIG. 4, a schematic illustration of an in-vivo device 400 with one or more sensors, a photodiode switch and a detachable part in accordance with an exemplary embodiment of the invention. Device 400 may be an in-vivo sensor that includes a detachable lobe, such as a heavy part 404, and a light part 402. Light part 402 may include one or more sensors such as for example one or more imagers 410 that may be located for example on opposing ends or sides of light part 402. One or more viewing windows 21 may be provided to enable, for example, capturing of images of the body lumen. Other or additional sensors may also be included, and sensors may be situated on other parts of light part 402. One or more sensors such as for example imaging sensors in light part 402 may include one or more illumination elements 406 and an optical imaging system that may include for example a lens 408 and an imager 410 such as for example a CMOS imager. Light part 402 may in some embodiments also include a counter 412 that may include for example a timer. Counter 412 may be capable of tracking the time that has elapsed since a certain event such as for example the introduction of device 400 into a body or some other event. Counter 412 may be connected to illumination device 406 or other components of device 400 by for example wires 411 or other circuitry. In alternate embodiments wireless communication may be possible between different components within device 400.

In some embodiments, heavy part 404 of device 400 may be attached to light part 402 by way of for example fasteners 414. Fasteners 414 may be, include or rely upon for example wires, fuses, such as for example burnable fuses, filaments, such as for example degradable filaments, glue, magnets or other items that may detachably or releasably hold heavy part 404 onto for example a fixed position of light part 402. Heavy part 404 may partially obstruct or overlap one or more of the viewing windows 21. Heavy part 404 may in some embodiments include a power source 416 such as a battery or other power source, a switch 418 that may be part of or included in for example a photodiode sensor or other light-sensitive sensor, and wiring 420 that may connect or link power source 416, switch 418, fasteners 414 or other components. Alternatively, the components may be connected through a wireless connection, such as by microwave, blue tooth communication, etc.

In some embodiments, a signal may be generated by for example counter 412, and such signal may activate, for example one on more of illumination devices 406. Illumination devices 406 such as for example those that face heavy part 402 may have been off or inactive until such signal was generated. In response to a signal, one or more of illumination devices 406 may emit light. Such light pass through a viewing window 21 and may be detected by for example a photosensitive sensor or switch 418. In response to the light that it detects, for example from illumination device 406, switch 418 may signal for example power source 416 to apply for example heat, electricity or some other force to release fasteners 414. The release of fasteners 414 may detach or free heavy part 404 from light part 402.

In some embodiments the signal from for example counter 412 or some other source may be generated in response to the passage of time, such as for example the passage of the approximate time that may lapse between the ingestion of device 400 and its arrival at a particular body lumen or organ such as for example the colon or cecum (e.g., 6-8 hours from ingestion, or other suitable time periods). In other embodiments, a signal may be generated in response to other events or stimulus that may occur or be provided from inside device 400 or from sources external to device 400.

Figure 5:
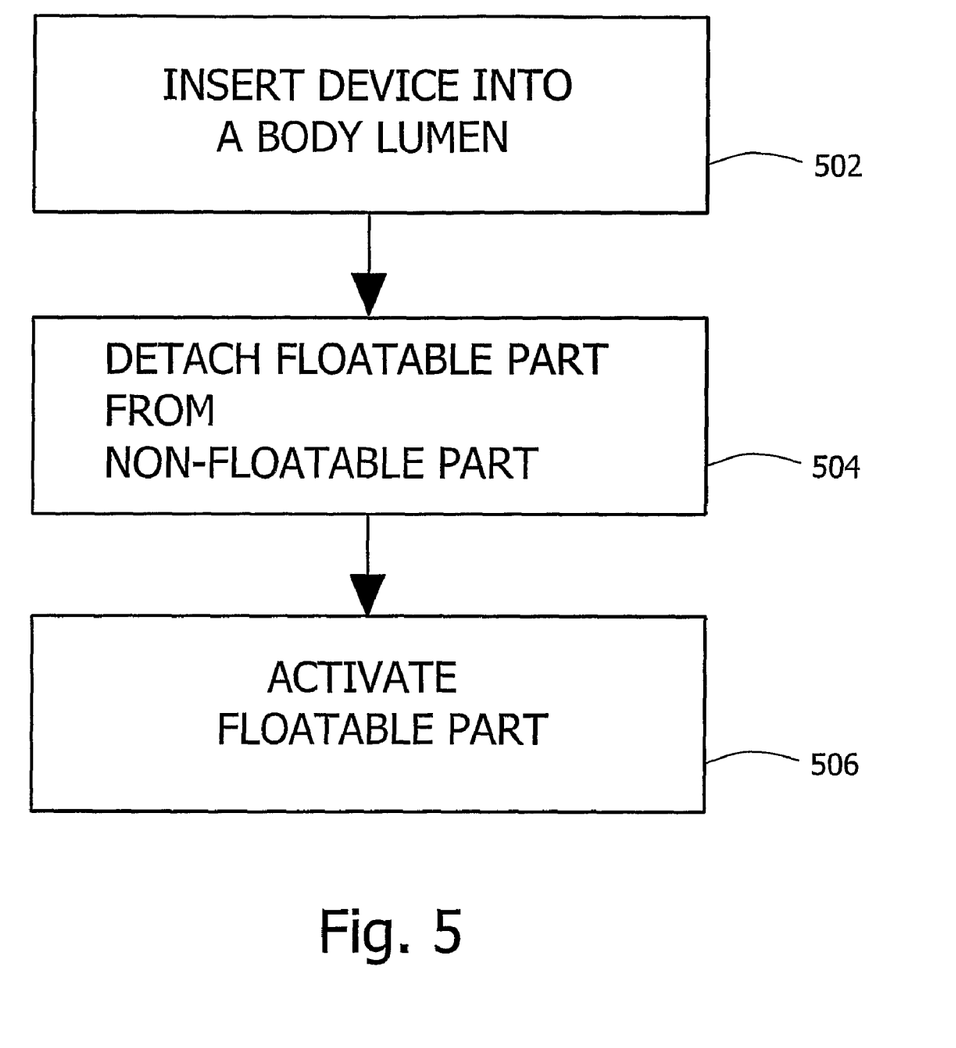
FIG. 5 is a flowchart schematically illustrating a method for in-vivo sensing of a lumen, according to an embodiment of the invention.

According to some embodiments of the invention there is provided a method for sensing a lumen such as, for example, the large intestine. A method according to one embodiment is schematically described in FIG. 5. In one embodiment an in-vivo sensing device which may include, for example, a floatable part and a non floatable part which may be releasably connected, may be inserted into a patient's GI tract (502), typically by ingestion. According to one embodiment, the in-vivo sensing and or imaging device, may be activated or not upon ingestion. According to some embodiments, activation of the device may be achieved, for example, as described herein. After a time period which may be indicative of the device having arrived at designated location, e.g., the patient's cecum (e.g., 6-8 hours after ingestion) the floatable and non floatable parts may be caused to become detached from each other (504). According to some embodiments a signal may be generated which may trigger or cause the two parts to become detached. According to some embodiments the detachment may be caused in response to indications other than time. For example, a motion detector, which may be included in the device, may indicate, by showing the device may not be in motion that the device has arrived in the cecum and a signal may then be generated to cause detachment. Other suitable destinations or marker points, other than the cecum, may be used. Further, other lumens, other than the large intestine, may be targeted. Upon detachment of the two parts the floatable part, which may include in-vivo sensing capabilities, may be activated (506) thus enabling the floatable part, which will be easily transported through at least parts of the large intestine, to sense (e.g., in one embodiment image) the large intestine. In alternate embodiments, other parts, such as a non-floatable part, may be activated for sensing.

While the invention has been described with respect to a limited number of embodiments, it will be appreciated that many variations, modifications and other applications of the invention may be made which are within the scope and spirit of the invention. The scope of the present invention is defined by the claims.

The invention claimed is:

1. An in-vivo sensing device for sensing in the gastrointestinal tract of a patient comprising:
   a first part having a specific gravity of less than one or approximately one;
   a second part having a specific gravity of more than one; and
   a fastener detachably connecting the first part and the second part, said fastener configured to detach the first part and the second part during the passage of said device through said gastrointestinal tract;
   wherein, when the first part and second part are connected, the specific gravity of the device is greater than one.

2. The in-vivo sensing device according to claim 1 wherein the specific gravity of the first part is less than the specific gravity of a bodily fluid within a body lumen.

3. The in-vivo sensing device according to claim 1 comprising an imager and an illumination source.

4. The in-vivo sensing device according to claim 1 wherein said fastener comprises a filament.

5. The in-vivo sensing device according to claim 1 wherein said fastener comprises a magnet, to temporarily attach the first part and the second part by an electromagnetic force.

6. The in-vivo device according to claim 1 wherein the first part is configured to detach in-vivo from the second part based on a predetermined parameter.

7. The in-vivo sensing device according to claim 6, wherein the predetermined parameter is a lapse of a predetermined period of time or a sensed environmental condition.

8. The in-viva sensing device according to claim 7, wherein the sensed environmental condition is a body temperature, an exposure to a certain liquid in a body lumen, or a pH level.

9. The in-vivo sensing device according to claim 1, wherein the first part is activated upon detachment from the second part.

10. The in-vivo sensing device according to claim 1, wherein the second part is activated upon detachment from the first part.

11. The in-vivo sensing device according to claim 1, wherein the first part or second part encapsulates medicaments that may be released upon the detachment of the second part or first part, respectively.

12. The in-vivo sensing device according to claim 1, wherein the first part and second part are caused to detach by ultrasound waves.

13. The in-vivo sensing device according to claim 1, wherein the in-vivo sensing device comprises a photodiode switch.

14. The in-vivo sensing device according to claim 1, wherein the in-vivo sensing device comprises a motion detector.

15. A system for in-vivo sensing comprising:
an in-vivo sensing device for sensing in the gastrointestinal tract of a patient comprising:
  a first part having a specific gravity of less than one or approximately one;
  a second part having a specific gravity of more than one; and
  a fastener detachably connecting the first part and the second part, said fastener configured to detach the first part and the second part during the passage of said device through said gastrointestinal tract;
  wherein, when the first part and second part are connected, the specific gravity of the device is greater than one;
an external receiver to receive wireless signals from the in-vivo device.

16. The system according to claim 15 comprising an in-vivo imager.

17. The system according to claim 15 comprising an external transmitter for transmitting signals to the in-vivo device.

18. The system according to claim 17 wherein the external transmitter is an ultrasound transmitter.

19. The system according to claim 15 comprising a display to display sensed data from the in-vivo sensing device.

* * * * *